United States Patent
Dietl

(10) Patent No.: US 11,173,055 B2
(45) Date of Patent: Nov. 16, 2021

(54) METHOD FOR SETTING UP A CONTROL AND TECHNICAL ORTHOPEDIC DEVICE

(75) Inventor: Hans Dietl, Gablitz (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 0 days.

(21) Appl. No.: 13/380,623

(22) PCT Filed: Jun. 11, 2010

(86) PCT No.: PCT/EP2010/003508
§ 371 (c)(1),
(2), (4) Date: Dec. 23, 2011

(87) PCT Pub. No.: WO2010/149276
PCT Pub. Date: Dec. 29, 2010

(65) Prior Publication Data
US 2012/0101596 A1 Apr. 26, 2012

(30) Foreign Application Priority Data
Jun. 23, 2009 (DE) .......................... 102009030217.4

(51) Int. Cl.
| | | |
|---|---|---|
| *A61F 2/72* | (2006.01) | |
| *A61F 2/76* | (2006.01) | |
| *A61F 2/70* | (2006.01) | |
| *A61F 2/54* | (2006.01) | |

(52) U.S. Cl.
CPC .................. *A61F 2/72* (2013.01); *A61F 2/54* (2013.01); *A61F 2/76* (2013.01); *A61F 2002/701* (2013.01); *A61F 2002/704* (2013.01)

(58) Field of Classification Search
CPC ........ A61F 2/72; A61F 2002/704; A61F 2/68; A61F 2002/6827; A61F 2/54; A61B 5/04888
USPC ....................................... 623/25, 57
See application file for complete search history.

(56) References Cited

U.S. PATENT DOCUMENTS

| | | | | |
|---|---|---|---|---|
| 3,491,378 | A * | 1/1970 | Dmitrievich et al. | .......... 623/25 |
| 3,631,542 | A * | 1/1972 | Potter | ............................. 623/25 |
| 4,030,141 | A * | 6/1977 | Graupe | ..................... A61F 2/68 |
| | | | | 623/25 |

(Continued)

FOREIGN PATENT DOCUMENTS

| | | |
|---|---|---|
| DE | 3609777 A1 | 9/1987 |
| WO | 0113778 A2 | 3/2001 |

(Continued)

OTHER PUBLICATIONS

Dupont, Anne-Caroline, et al., "A Myoelectric Control Evaluation and Trainer System," IEEE Transactions on Rehabilitation Engineering, vol. 2, No. 2, pp. 100-107, Jun. 1994.

(Continued)

*Primary Examiner* — Bruce E Snow
*Assistant Examiner* — Melissa A Hoban
(74) *Attorney, Agent, or Firm* — Holland & Hart LLP

(57) ABSTRACT

The invention relates to a method for setting up a control, and to a control for a technical orthopedic device, and a technical orthopedic device as such. Actuations of the technical orthopedic device (1) are provided by means of an output device (2, 3), biomettric signals are received by sensors (12), and said signals are associated with the respective actuations.

6 Claims, 2 Drawing Sheets

(56) References Cited

U.S. PATENT DOCUMENTS

Figure 1:
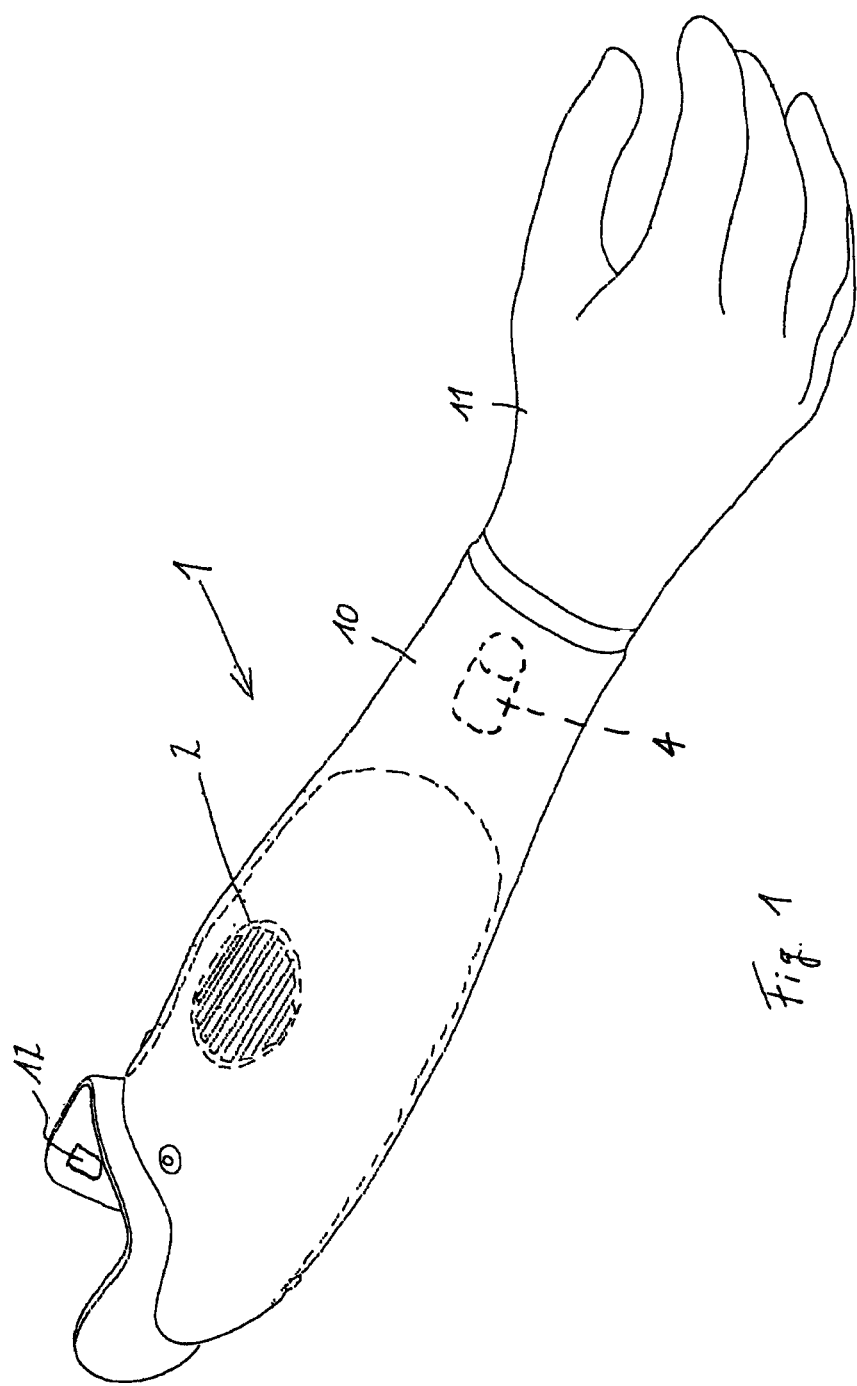

| | | | |
|---|---|---|---|
| 4,808,187 A * | 2/1989 | Patterson et al. ............... | 623/25 |
| 5,413,611 A * | 5/1995 | Haslam et al. ................. | 623/25 |
| 5,748,845 A * | 5/1998 | Labun ................ | A61N 1/36003 |
| | | | 607/66 |
| 2004/0106881 A1 | 6/2004 | McBean et al. | |
| 2006/0155386 A1* | 7/2006 | Wells et al. .................... | 623/25 |
| 2006/0167564 A1* | 7/2006 | Flaherty et al. ............... | 623/57 |
| 2009/0024062 A1 | 1/2009 | Einarsson | |
| 2010/0030341 A1* | 2/2010 | Dietl et al. ...................... | 623/25 |
| 2011/0134139 A1 | 6/2011 | Brandmayr et al. | |

FOREIGN PATENT DOCUMENTS

| | | |
|---|---|---|
| WO | 0249534 A2 | 6/2002 |
| WO | 2006086504 A2 | 8/2006 |
| WO | 2008005865 A1 | 1/2008 |
| WO | 2008036746 A2 | 3/2008 |
| WO | 2009032937 A2 | 3/2009 |
| WO | 2009145969 A2 | 12/2009 |
| WO | 2010015305 A1 | 2/2010 |

OTHER PUBLICATIONS

Jun-Uk Chu, "A Supervised Feature-Projection-Based Real-Time EMG Pattern Recognition for Multifunction Myoelectric Hand Control," IEEE/ASME Transactions on Mechatronics, vol. 12, No. 3, pp. 282-290, Jun. 2007.
PCT International Search Report for PCT International Application No. PCT/EP2010/003508, dated Oct. 22, 2010.

* cited by examiner

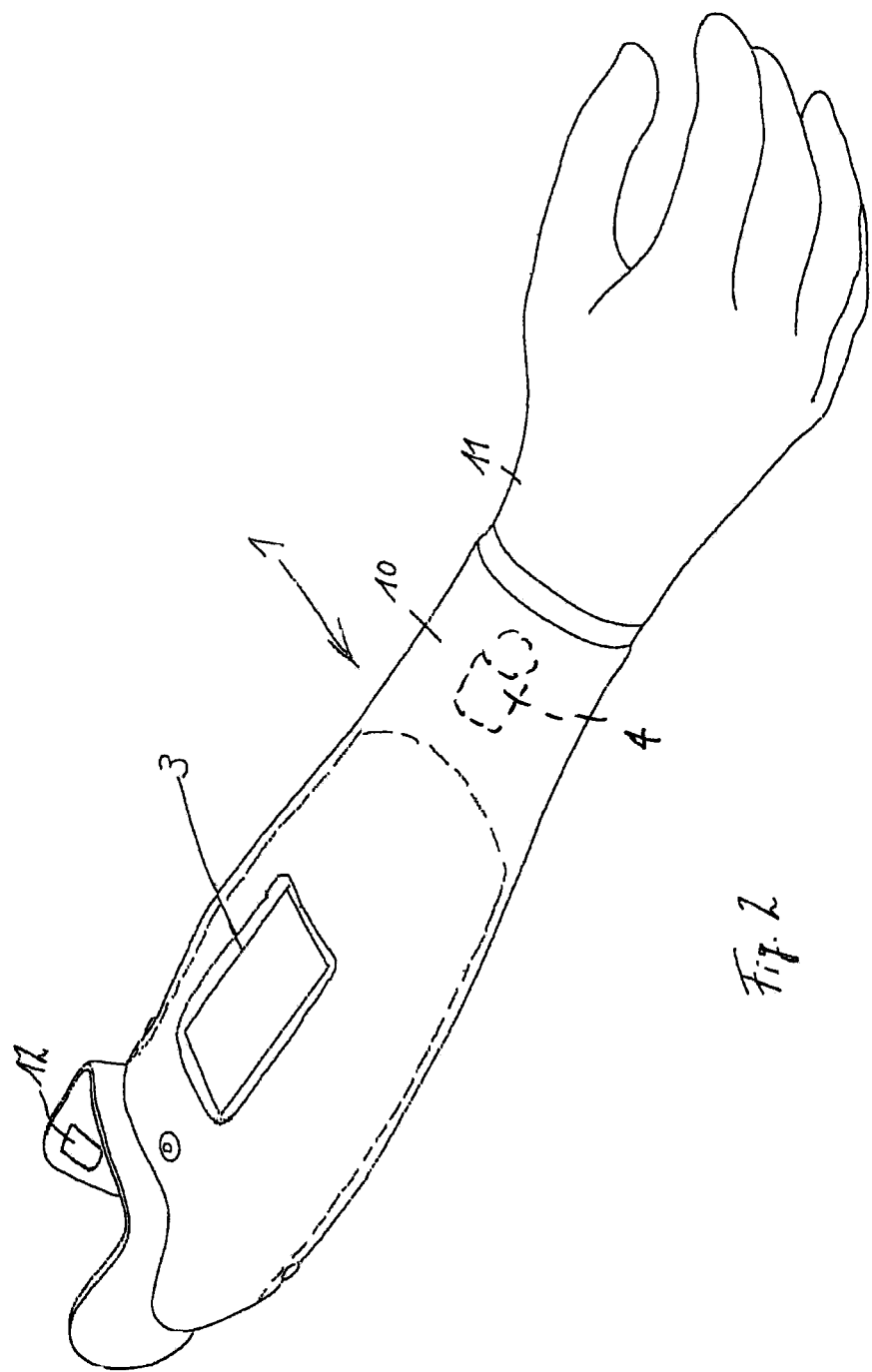

METHOD FOR SETTING UP A CONTROL AND TECHNICAL ORTHOPEDIC DEVICE

The invention relates to a method for setting up a control of a technical orthopedic device, which is placed against a body part of a patient and connected to sensors recording biometric data of a patient, a control of the technical orthopedic device, and also a technical orthopedic device as such.

Driven technical orthopedic devices, such as prostheses or orthoses, require control signals so that the motor-driven drives operate as desired. By way of example, these control signals are produced via collector electrodes, which record myoelectric signals, which, after a possibly required amplification by a control device, are used as impulses for activating drives. The conventional method for associating the myoelectric signals with the respective drives consists of associating an electrode with individual muscles or muscle groups and associating a command for activating or deactivating a drive with each myoelectric signal generated by said muscle group. So as to be able to operate the technical orthopedic device, e.g. the prosthesis, correctly, a great deal of training is generally required so that the user of the technical orthopedic device produces the correct control command by activating the applicable muscles or muscle groups. The method, which, in principle, is comparable, emerges during the use of implanted electrodes, with implanted electrodes making it possible to implement a greater number of signals and hence a greater number of control channels. In the case of a prosthetic application, the result of this is that, in order to carry out particular commands, muscles or muscle groups, which would not be activated in the case of healthy limbs, need to be activated. The muscle groups required to close a hand are predominantly situated in the forearm; if no forearm muscles are present anymore, the corresponding signals must be produced by other muscle groups, which means comprehensive relearning for the user, requiring extraordinary amounts of time and much practice.

An object of the present invention is to provide a method for setting up a control of a technical orthopedic device, a control for a technical orthopedic setting and also a technical orthopedic device as such, by means of which the technical orthopedic device can be operated more quickly and more easily using biometric data recorded by sensors.

According to the invention, this object is achieved by a method having the features of the main claim. Advantageous embodiments and developments of the invention are listed in the respective dependent claims.

The method for setting up a control of a technical orthopedic device, which is placed against a body part of a patient and connected to sensors recording biometric data, at first provides for outputting a representation of an actuation of a limb in order thereby to invite a patient to carry out this actuation. Thus, the patient is actively urged to carry out a specific movement that can be carried out by the technical orthopedic device. The patient then carries out the movement in a virtual fashion; i.e., the patient activates those muscle groups that should individually be contracted or relaxed by the patient for carrying out the natural movement. The biometric signals, e.g. muscle contractions or electrical impulses in the tracts of nerves, which are produced by the patient after the invitation as a willing, voluntary reaction, are captured by the sensors and associated with the activity carried out. Here, the association is with that actuation that the patient was invited to carry out. This signal association between the produced signals and the actuation carried out and to be carried out is stored. In this claimed method, the control is no longer set up in a rigid fashion where the patient must activate precisely the one muscle that is associated with the respective actuation; rather, there is an individual association between the signals and the respective actuation. The problem addressed by this method is that of possible changes in myoelectric signal patterns over time, for example as a result of muscular atrophy or other changes in the muscular system. In the case of conventional methods, it is necessary to subject the patient to new training so that precisely one muscle or muscle activation signal is filtered out for carrying out precisely one command or function. The claimed method renders it possible to carry out signal pattern recognition, which is based on a plurality of sensor values, and so the pattern recognition overall renders it possible to actuate a larger number of functions than in the case of conventional methods.

The method preferably provides for the technical orthopedic device to be applied to a body part of the patient in order to create a situation that is as realistic as possible when setting up the control. In principle, it is also possible that only the sensors are applied to the respective body part, while the technical orthopedic device, which, for example, is embodied as a prosthesis, orthosis, as training equipment or as a stimulation device, is situated at a distance from the patient. In addition to prosthetics and technical orthopedics, the method can also be used within the scope of rehabilitation, after an accident or surgery or other damage to the musculoskeletal system. It is also possible to act within the scope of an electro-stimulation and also activate muscles by means of additional impulses as an alternative or in addition to the activation of drives.

According to the invention, provision is made for the representation of the actuation to be carried out to be output in an acoustic and/or tactile fashion and/or on a display. Each output mode of a representation has specific advantages. An acoustic representation of the actuation to be carried out can be perceived without problems in poor lighting conditions and also by patients with poor vision. A tactile output renders it possible to output a multiplicity of complex signals in order to transmit corresponding information to the user. In addition to vibrations or vibration patterns, it is possible to stimulate the skin of the user using electrical impulses. It is likewise possible to output temperature signals, for example by heating or cooling. These signals can be output very inconspicuously. An indication on a display allows inconspicuous transmission of information to the patient, and so the control can also be set up in public without being very conspicuous. Provision is also made for it to be possible to select the type of representation. Provision is likewise made for the combination of all types of representations, and so, in addition to an optical representation, there is also a tactile and/or acoustic representation of the actuation to be carried out. The optical representation can either be brought about in the form of a text message or by a visualization of the actuation, e.g. by displaying a closing hand, a hand rotation or a flexing or stretching of a lower leg. It is self-evident that the patient cannot carry out the actuation as such in the case of a prosthetic application since the prosthesis serves as a replacement for a missing limb. Instead of an actual movement, the patient carries out a muscle contraction or a nerve impulse, which in his opinion and according to his movement memory, corresponds to that movement that needs to be carried out for the actuation. This results in a signal pattern that is captured by the sensors, without an actual movement needing to be carried out.

A development of the invention provides for the data to be recorded by sensors, which are arranged on the skin surface or implanted into the patient. The technical orthopedic device can be activated by putting one or more drives into operation such that the prosthesis, the orthosis, the training equipment or the rehabilitation device carries out the desired movement or the desired actuation in an operating mode of the technical orthopedic device after recalling a stored signal pattern.

As an alternative to activating by means of drives or by means of a drive, or in addition thereto, provision is made for the activation to be brought about by electro-stimulation of muscles connected to the actuation. This renders it possible to link specific movement patterns to specific muscle actuations, and thus learn motions or improve or maintain coordinative capabilities.

The method can furthermore provide for different actuations to be output in succession, and so, for example, an actuation spectrum is successively prescribed and worked through. Every prescribed actuation, which is output to the patient via the output device, is associated with a specific signal or a specific signal pattern. If the signal or signal pattern is sufficiently unique, the next actuation is output. In the process, it is possible, and provision is made therefor, that each actuation be output a number of times in order to obtain confirmation of the signal or the signal pattern. Provision is likewise made for a signal range to be formed from the associated signals when the actuation is output a number of times, with an activation signal having to lie in said signal range in order to trigger the activation of the associated actuation. This renders it possible to trigger the desired actuation of the technical orthopedic device, even in the case of fuzzy signals. Outputting the invitation in respect of an actuation a number of times in succession increases the uniqueness of the signal association because statistical averaging of the signals can be achieved as a result of the relatively large number of recorded biometric signals, as a result of which individual outliers are not given undue attention.

The method for controlling a technical orthopedic device, in which the control was initially set up as described above, provides for sensor signals from the sensors captured after the set-up of the control to be compared to the stored signal association and the technical orthopedic device to be activated to carry out the actuation associated with the signal if sufficient correspondence is determined between the captured signals and the stored signal association. This renders it possible to operate a technical orthopedic device in which the control adapts to the respective current needs and conditions of the patient. This affords the possibility of taking account of current changes in the movement behaviour or in the activation properties of the muscles, remaining muscles or the biometric variables associated with the sensors. Rather than train a patient in respect of a fixed control, the control is adapted to the respective patient. A multiplicity of sensors renders it possible to capture a very wide range of sensor signal patterns, and so control is possible by initiating partly complex, virtual movements, which, for example in the case of amputations, must remain without actual effects on the actuation to be carried out.

The technical orthopedic device for carrying out the methods as claimed in one of the preceding claims, with attachment means for attaching it to a body part, at least one actuator, at least one sensor device and a control device, provides for an output device to be arranged on the technical orthopedic device, which output device outputs representations of actuations of the technical orthopedic device that should be carried out by the patient or the technical orthopedic device. The output device can be fixedly installed on the technical orthopedic device or be attached to the latter in a releasable fashion. In principle, it is also possible merely to connect the technical orthopedic device to the output device when necessary, for example by cables or a radio link, so that the technical orthopedic device as such can have the smallest and lightest design possible.

The output device is preferably designed as a display, sensory stimulator and/or loudspeaker and can be arranged on the technical orthopedic device either as a fixed or temporary component. A sensory stimulator is understood to mean devices, by means of which sensory perceptions can be generated, for example tactile agents that produce a vibration pattern or a pressure or pressure pattern. It is also possible to use warmth and coldness, electrical impulses or other surface responses as an output device. In principle, provision is made for the output device to be designed as a component of the technical orthopedic device; that is to say e.g. the prosthesis, orthosis, a functional textile, the rehabilitation equipment or the training equipment.

The actuator can be designed as a motor and/or as a muscle-stimulating device. A motor-driven drive is provided in the case of prostheses and devices, when the muscles can develop no, or only very little, power; an alternative or additional muscle-stimulating device in the form of electrodes that bring about a contraction of the corresponding muscles can be provided in order to produce a training effect or to amplify the latter or to obtain therapeutic successes.

The sensors for capturing biometric data can be designed as collector electrodes and/or stimulation electrodes; it is likewise possible to provide intracorporeal electrodes or to capture the biometric data in a different fashion.

In the following text, an exemplary embodiment of the invention will be explained in more detail on the basis of the attached figures.

In detail:

FIG. 1 shows a perspective, schematic illustration of a first embodiment of the technical orthopedic device; and FIG. 2 shows a variant of the embodiment as per FIG. 1.

FIG. 1 shows a perspective, schematic illustration of a forearm prosthesis 1 with a forearm shaft 10 and a prosthetic hand 11 at the distal end of the forearm shaft 10. Provision can be made within the forearm shaft 10 for control devices, energy storages and motor-driven drives 4, as shown in FIGS. 1 and 2, for actuating the prosthetic hand 11; it is likewise possible, and provision is made therefor, that at least some of this equipment is also arranged in the prosthetic hand 11. The prosthetic hand 11 as a whole can be moved in the region of the wrist, with both external rotation and internal rotation, and also flexion and extension, of the prosthetic hand 11 being possible. The fingers of the prosthetic hand 11 can likewise be embodied in an actuatable fashion, particularly the thumbs and index and middle fingers so that the essential types of grip can be carried out.

On the prosthetic shaft 10 in the illustrated embodiment, collector electrodes 12 are also arranged on the proximal, open end of the forearm shaft 10. These sensors 12 record biometric data, myoelectric signals in the present case, which are transmitted by said sensors to the control electronics (not illustrated) for actuating the drives. In principle, it is also possible that other sensors are provided, the signals of which are then sent to the control electronics via cables or a radio link.

An output device 2 in the form of a loudspeaker is arranged on the outside of the prosthetic shaft 10 in FIG. 1; this loudspeaker is used to invite the prosthesis user to produce a specific pattern of biometric data signals. The invitation is brought about by virtue of the fact that the actuation of the prosthetic device 1 to be carried out is reproduced, for example by the acoustic representation "close hand" or "open hand". After outputting the actuation to be carried out by the prosthesis, the sensor signal or sensor pattern of a plurality of sensors is recorded in a learn mode, and these recorded sensor signals or sensor patterns are associated with the respective actuation. This procedure is repeated for each actuation until there is sufficient uniqueness of the sensor signal or the sensor signal pattern. Once all possible or desired actuations are associated with a sensor signal or sensor signal pattern, the learn mode is completed. Then, in an activation mode, the actuations are carried out by the prosthetic hand if the signal pattern associated with the respective actuation is captured by the sensors 12 and evaluated in the control unit.

Individual adaptation of the control by means of the sensor signals from the respective patient is thus undertaken every time the control is set up, for example every time the prosthesis 1 is put on again. This makes it easy to understand changes in the patient such that the control adapts to the patient and the patient need not adapt to the control.

The acoustic output device 2, which is designed as a speech module or loudspeaker, can be fixedly connected to the prosthesis shaft 10; alternatively, the output device 2 can be arranged on the prosthesis shaft 10 in a removable fashion.

FIG. 2 illustrates a variant of the invention, in which the basic design of the prosthesis device 1 corresponds to the one in FIG. 1. Instead of a loudspeaker of the 2 as output device, a display 3 is arranged in the prosthesis shaft 1, and so there is an optical representation instead of an acoustic representation of the actuation. By way of example, this representation can be brought about by a text display or images or film representations. Here too, provision is made for the display 3 to be attached to the prosthesis shaft 10 in a removable fashion. In principle, it is also possible to combine acoustic and optical output devices 2, 3 with one another; it is also possible, and provision is made therefor, that a switch can be made between the various display types.

The invention claimed is:

1. A method for setting up a control of a technical orthopedic device and operating the technical orthopedic device, the technical orthopedic device configured to be placed against a body part of a patient and connected to sensors operable to record biometric data from muscles of the body part, the technical orthopedic device being an orthotic device or a prosthetic device, the biometric data including biometric signals, the method comprising:
   outputting a representation of an actuation of a limb as an invitation to the patient to carry out this actuation, the representation being output as at least one of an acoustic, a tactile stimulus, or a display, the limb comprising the body part or formerly extending from the body part;
   capturing, with the sensors, the biometric signals from muscles of the body part, the biometric signals being produced by the patient as a voluntary reaction in response to the invitation, the biometric signals defining a first signal pattern;
   associating the produced biometric signals with the actuation invited to be carried out;
   storing the signal association;
   after storing the signal association:
   capturing, with the sensors, additional biometric signals from the muscles of the body part, the additional biometric signals defining a second signal pattern;
   determining whether the second signal pattern matches the first signal pattern;
   activating the technical orthopedic device based on the stored signal association and the second signal pattern matching the first signal pattern; and
   electro-stimulating muscles connected to the actuation of the limb.

2. The method as claimed in claim 1, further comprising placing the technical orthopedic device against the body part of the patient.

3. The method as claimed in claim 1, wherein the biometric data is recorded by sensors implanted into the patient.

4. The method as claimed in claim 1, wherein the technical orthopedic device is activated by putting one or more drives into operation.

5. The method as claimed in claim 1, wherein different actuations are output in succession.

6. The method as claimed in claim 5, further comprising
   outputting additional representations of the actuation of the limb as an invitation to the patient to carry out this actuation, and capturing, with the sensors, the biometric signals from muscles of the body part produced by the patient in response to the additional representations of the actuation, the biometric signals defining a range of first signal patterns; and
   activating the technical orthopedic device based on the stored signal association and the second signal pattern being within the range of first signal patterns.

\* \* \* \* \*